(12) United States Patent
Strissel et al.

(10) Patent No.: US 6,935,584 B2
(45) Date of Patent: Aug. 30, 2005

(54) USES OF WHITE CORN HYBRIDS

(75) Inventors: Jerry F. Strissel, Harlan, IA (US); Michael J. Stiefel, Panora, IA (US); Dale Ball, Harlan, IA (US)

(73) Assignee: Syngenta Seeds, Inc., Golden Valley, MN (US)

( * ) Notice: Subject to any disclaimer, the term of this patent is extended or adjusted under 35 U.S.C. 154(b) by 0 days.

(21) Appl. No.: 10/106,829

(22) Filed: Mar. 27, 2002

(65) Prior Publication Data

US 2003/0066106 A1 Apr. 3, 2003

Related U.S. Application Data (60) Provisional application No. 60/279,145, filed on Mar. 27, 2001, and provisional application No. 60/356,758, filed on Feb. 15, 2002.

(51) Int. Cl.[7] ................................................. B02C 9/00
(52) U.S. Cl. ................................. 241/9; 241/12; 241/21
(58) Field of Search ............................. 241/6, 8, 9, 12, 241/21

(56) References Cited

U.S. PATENT DOCUMENTS

| | | | | |
|---|---|---|---|---|
| 3,909,288 A | * | 9/1975 | Powell et al. ................. | 127/68 |
| 3,928,631 A | * | 12/1975 | Freeman et al. .............. | 426/18 |
| 4,181,748 A | * | 1/1980 | Chwalek et al. ............. | 426/623 |
| 5,254,673 A | * | 10/1993 | Cook et al. ................. | 530/373 |
| 5,410,021 A | * | 4/1995 | Kampen ..................... | 530/372 |
| 5,932,018 A | * | 8/1999 | Palardy ....................... | 127/67 |
| 5,968,585 A | * | 10/1999 | Liaw et al. ................. | 426/656 |
| 6,184,002 B1 | * | 2/2001 | Mitchinson et al. .......... | 435/99 |
| 6,368,649 B1 | * | 4/2002 | van Bommel .............. | 426/482 |
| 6,531,648 B1 | * | 3/2003 | Lanahan et al. ............ | 800/278 |

OTHER PUBLICATIONS

T.W. Crowe, S.K. Singh, and L.A. Johnson, "Wet–Milling Properties of 20 White Corn Hybrids", Center for Crops Utilization Research. Iowa State University, Ames, Iowa 50011.

Corn: Chemistry and Technology, Second Edition, White, Pamela J. and Johnson, Lawrence A., pp. 344–347 and 476–479.

Darrah et al, *White Food Corn* : 1999 Performance Tests Agricultural Research Service, U.S. Department of Agriculture; Agricultural Experiment Station, University of Missouri–Columbia; Special Report 528, 12/99/2.4M.

Zimmerman Brand [brochure], "White Corn; 1999–2000", Wilson Genetics, L.L.C.

* cited by examiner

*Primary Examiner*—Mark Rosenbaum
(74) *Attorney, Agent, or Firm*—Bruce Vrana (57) ABSTRACT

The present invention provides hybrid white corn that produces grain with novel compositional characteristics, such as, higher endosperm protein concentration and low levels of carotenoids. The compositional changes facilitate the use of an improved process for wet milling of white corn and improve the characteristics and performance of the products derived therefrom. A high protein, nearly carotene-free corn gluten meal and substantially pure starch are extracted from this white corn having a unique genotype, a unique kernel phenotype and advantage in the wet milling process is disclosed.

10 Claims, 4 Drawing Sheets

USES OF WHITE CORN HYBRIDS

CROSS REFERENCE

This application is related to U.S. provisional application Ser. No. 60/279,145 filed Mar. 27, 2001 and U.S. provisional application Ser. No. 60/356,758 filed Feb. 15, 2002.

FIELD OF INVENTION

The present invention relates to the general fields of genetics, plant physiology, grain composition, and specifically to the novel use of white corn hybrids in the wet milling process. This application further relates to novel white corn hybrids providing enhanced compositional characteristics, increased yields of critical components useful for novel end-product uses, and potential for reducing processing waste by-products in the wet milling process. The novel white corn products provide enhanced characteristics for feed applications, especially aqua culture.

BACKGROUND OF THE INVENTION

Corn (Zea mays L.) has a monoecious flowering habit. The male and female flowers are separate but develop on the same plant. The staminate (male) flowers are borne in the tassel and the pistillate (female) flowers are borne on the ears. Corn is predominantly cross-pollinated; pollen from any tassel randomly pollinates the silks on the ears of adjacent plants or even its own silks. The average corn tassel produces 25 million pollen grains, and most ears have 500–1200 kernels.

The development of corn varieties in the early 1900s was dependent on mass selection. This technique involves no pollen control; each ear is pollinated by a random mixture of pollen from neighboring plants in the field. Therefore, selection progress is slow. However, this technique is effective for simply inherited characteristics, such as, ear and plant height, ear number, adaptation, maturity, and kernel and ear characteristics. Grain yield improvement by mass selection is more difficult because random pollination involves both good and poor yielding plants. Also, the effects of genotype and environment cannot be separated using mass selection techniques.

Alternatively, corn breeders employ controlled pollination, artificial selection and genetic analysis to develop numerous genetic lines or varieties of corn displaying a plethora of desired traits, e.g., yield potential, maturity time, disease resistance, insect resistance, ear size, plant height, drought tolerance. Established inbred lines are used as starting material for further crossing, selection, and analysis in order to develop additional varieties. G. H. Shull (1909), of the Carnegie Institute, has been given credit for suggesting the development of pure inbred lines in corn. The method of inbred line development involves self-fertilization (selfing) of open-pollinated varieties and selection of homozygous biotypes. Inbred lines are generally not vigorous, and yields are low. Over time, breeders improve the elite older inbred lines through recycling. Also, new lines are developed from synthetics and populations improved by some form of recurrent selection. The resulting inbred lines from these sources have more vigor, tolerate greater stress by increased plant densities, and have increased yields. More specifically, plants that have been self-pollinated and selected for type for many generations become homozygous at almost all gene loci and produce a uniform population of true inbred breeding progeny. A cross between two different homozygous inbred lines (single cross hybrid) produces a uniform population of hybrid plants that may be heterozygous for many gene loci.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male) and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in corn plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile corn and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511, the disclosures of which are specifically incorporated herein by reference. There are many other methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (EPO 89/3010153.8 and WO 90/08828).

Another system useful in controlling male sterility makes use of gametocides. Gametocides are not a genetic system, but rather a topical application of chemicals. These chemicals effect cells that are critical to male fertility. The application of these chemicals effects fertility in the plants only for the growing season in which the gametocide is applied (see, U.S. Pat. No. 4,936,904 to Carlson, specifically incorporated herein by reference). Application of the gametocide, timing of the application and genotype specificity often limit the usefulness of the approach.

The use of male sterile inbreds is but one factor in the production of corn hybrids. The development of corn hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced: $F_1$ to $F_2$; $F_2$ to $F_3$; $F_3$ to $F_4$; $F_4$ to $F_5$, etc.

In particular, a single cross hybrid results from the cross of two inbred lines, each of which has a genotype that complements the genotype of the other. The hybrid progeny of the first generation is designated $F_1$ and exhibit hybrid vigor, or heterosis, in relation to their inbred parents. Hybrid vigor may be manifested in polygenic traits, such as, increased vegetative growth and increased yield. It is these hybrids that are generally sought in commercial development. That is to say, an objective for commercial corn hybrid development is to produce new inbred lines that combine to produce superior agronomic performance.

Typically, the development of a hybrid corn variety involves three steps: 1) the selection of plants from various germplasm pools for initial breeding crosses; 2) the selfing of the selected plants from the breeding crosses for several generations to produce a series of inbred lines, which, although different from each other, breed true and are highly uniform; and, 3) crossing the selected inbred lines with unrelated inbred lines to produce the hybrid progeny ($F_1$). Once created, a continual supply of hybrid seed can be produced using the inbred parents and the hybrid corn plants can be generated from the hybrid seed.

A single cross hybrid is produced when two inbred lines are crossed to produce the $F_1$ progeny. A double cross hybrid is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$), and consequently, seed from hybrids is not generally used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed. Once the seed is planted, it is possible to identify and select these self-pollinated plants. These self-pollinated plants will be genetically equivalent to the female inbred line used to produce the hybrid. Typically these self-pollinated plants can be identified and selected due to their decreased vigor. Female selfs are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1–8 (1995), the disclosure of which is expressly incorporated herein by reference. Through these technologies, the homozygosity of the self-pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritca si Aplicata Vol. 20 (1), p. 29–42.

Corn is an important field corp. Thus, a continuing goal of plant breeders is to develop consistently performing, high-yielding corn hybrids that are agronomically sound and based on stable inbred lines. The reasons for this goal are obvious: to maximize the amount of grain produced with the inputs used and minimize susceptibility of the crop to environmental stresses. While approximately 80% of today's corn crop is used to feed livestock, both in the United States and abroad, food and non-food products containing corn number greater than 3500 and are increasing. Corn is also a major source of product for the milling, both dry and wet, industry. Principal products of dry milling include, for example, grits, meal and flour. The principal products of wet milling include, for example, starch, fiber, corn syrup and dextrose. Corn oil recovered from the corn germ is a by-product of both dry and wet milling. Industrial and food applications of wet milling products of corn are based on the general functional and intrinsic properties of corn, such as viscosity, film formation, adhesive properties, taste, protein levels and starch types.

One of these milling products, starch, is comprised of two polymers (polysaccharides), amylose and amylopectin. In particular, starch derived from dent or flint corn is composed of approximately 73% amylopectin and 27% amylose, each of which does not exist free in nature, but as a component of a discrete, semi-crystalline aggregate, called starch granules. Amylose is an essentially linear polymer composed almost entirely of α-1-4 linked D-glucopyranose. Although typically illustrated as a straight chain structure for the sake of simplicity, amylose is actually often helical. The interior of the helix contains hydrogen atoms and is therefore hydrophobic, allowing amylose to form a type of clathrate complex with free fatty acids, fatty acid components of glycerides, some alcohols and iodine. Amylopectin, the predominant molecule in most starches is a branched polymer that is much larger than amylose. Amylopectin is composed of α-1-4 linked glucose segments connected by α-1-6 linked branch points.

Starch bearing plants, e.g., corn, produce different percentages of amylose and amylopectin, different size starch granules and different polymeric weights for both the amylose and amylopectin. The ratio of amylose to amylopectin within a given type of starch is an important consideration with respect to starch functionality in foods; differences in ratios produce markedly different physical and functional properties in the starch. That is, amylose and amylopectin content and structure affect the architecture of the starch granule, gelatinization and pasting profiles, as well as appearance and textural attributes. Heretofore, starch is typically physically and/or chemically treated to manipulate these and other characteristics. For example, for many industrial purposes, the pearl starch fraction is treated with chemicals to make the starch whiter.

Proteins, lipids, moisture and ash (minerals and salts) are also present in starch granules in minute quantities. Starch granule proteins are divided into two types on the basis of their ability to be extracted from the granules: surface and integral. Surface starch granule proteins are extracted with salt solutions, whereas integral starch granule proteins require more rigorous extraction, for example, with the detergent sodium dodecyl sulfate (SDS) or an alkaline solution. Integral proteins are embedded and may be covalently bound in the amylose-amylopectin structure of the granule, while the surface proteins are more loosely associated with the exterior of the granule. In order to separately recover either or both starch or protein components, the protein/starch matrix must be broken. In known processes for separating protein from starch, either steeping destroys the usefulness of protein and starch or the protein is ineffectively recovered.

Typically, corn used for industrial or food purposes is either dry milled or wet milled. Historically, wet milling has been primarily used to process yellow dent corn and the like. Traditionally, white corn varieties are known for their inefficiency or inability to be wet milled. Thus, the corn processing industry relies upon dry milling techniques to process white corn.

The objective of the dry milling process is to remove the bran coat and germ from the corn kernel while keeping the endosperm portion largely intact, a process which, traditionally, has not or has not efficiently been accomplished using a wet milling process. This separation yields prime products high in starch, low in oil, essentially free of bran and germ, and having excellent shelf life and stability. The dry milling process is comprised of several processing steps. Briefly, the incoming grain is cleaned and then moistened, or tempered, to loosen and toughen the bran coat and soften the germ to facilitate separation in the degerminator. The initial separation into the component parts begins in the degerminator, a specially designed attrition mill containing a truncated cone, surfaced with numerous pearling knobs, rotating inside a perforated housing. As the tempered kernels pass through this device, the abrading action peels the bran coat and germ away from the endosperm. The germ, hull, and small endosperm pieces pass through the perforations in the housing (hereinafter referred to as "through stock") and the larger endosperm pieces exit the end, or tail, of the degerminator (hereinafter referred to as "tail stock"). The remaining steps include aspiration, milling and sifting; and, drying and cooling. The end result is a spectrum of degermed corn products that includes flaking grits, corn flour, corn bran, corn oil and hominy feed. The degermed products are used in a wide variety of food and beverage applications, some of which include breakfast foods, malt beverages, snack food, prepared mixes, batter and breading mixes and low calorie/high fiber foods.

The wet milling process is used primarily to extract starch and gluten from corn. Other fractions that are a part of the by-products include the germ, fiber, and steep water. Generally, wet milling involves an initial water soak under controlled conditions to soften the corn kernels. The corn is then milled and its components separated by screening, centrifuging and washing. The first step in the actual processing is called steeping and includes controlled processing conditions such as temperature, time, and sulfur dioxide concentration. Steeping softens the kernels, facilitating separation of the corn components. The corn kernels are placed in a steeping tank with a countercurrent flow of water at about 120–125° F. The water is treated with sulfur dioxide ($SO_2$) to a concentration of 0.12–0.20% by weight. The sulfur dioxide increases the rate of water diffusion into the kernel and assists in breaking down the protein-starch matrix necessary for high starch yield and quality. The kernels remain in the steep tank for 24–50 hours. In general, 8–9 gallons of water/bushel of corn is required, with about 3.5 gallons/bushel being absorbed by the corn to increase its moisture from approximately 16% to 45% during steeping. The remainder, approximately 4.5–5.5 gallons/bushel, is removed from the system and must be dealt with in an environmentally acceptable manner. The kernels are then dewatered, and subjected to sets of attrition type mills to release the germ.

After the germ is recovered, the remaining kernel components including the starch, hull, fiber, and gluten are subjected to another set of attrition mills and passed through a set of wash screens to separate the fiber components from the starch and gluten. The starch and gluten pass through the screens while the fiber does not. Centrifugation or a third grind followed by centrifugation is used to separate the starch from the protein. Centrifugation produces a slurry which contains the starch granules which is dewatered, washed with fresh water, and dried to about 12% moisture. The amount of extractable starch has been one of the prime concerns of wet millers. It is dependent upon the ease of separation of the components, uniformity of the product, and the hardness of the endosperm. Yellow corn generally has a relatively hard endosperm, requiring a higher level of sulfur dioxide in the steeping process to separate the components. More sulfur dioxide results in more waste by-products requiring disposal.

Traditionally, the dry and wet milling industries have not selected corn hybrids for milling based on particular component profile of the hybrid kernels, for example, protein characteristic of the endosperm, an amino acid characteristic, a β-carotene characteristic, a xanthophyll characteristic, a starch characteristic, and combinations thereof. In fact, it is a common practice in the milling industry to mix together different corn varieties prior to milling in order to obtain more uniform end-products.

There is a need, therefore, to select white corn hybrids for wet milling based on particular grain components, for example, protein characteristic of the endosperm, an amino acid characteristic, a β-carotene characteristic, a xanthophyll characteristic, a starch characteristic, and combinations thereof. There is also a need to select particular white corn hybrids adapted for wet milling and potentially requiring the use of less steeping water and sulfur dioxide during the wet milling process. A further need is for an improved wet milling process for efficiently processing white corn hybrids.

Both environment and genetics affect the properties of corn for alkaline cooking. See, Bedolla, S. 1980, "Effect of genotype on cooking and texture of corn for tortilla production", M.S. thesis, Texas A&M University, College Station. See also, Goldstein, T. M. 1983, "Effect of environment and genotype on hardness and alkaline cooking properties of maize", M.S. thesis, Texas A&M University, College Station. In general, the properties desired in corn for alkaline cooking are: uniformly sized kernels of high density and high test weight. A high proportion of hard or flinty endosperm, intact kernels free of fissures or stress cracks, kernels without prominent dents in the crown, easily removed pericarp, clean yellow or white color, and white cobs instead of red.

Rate of cooking is affected by the relative rate of water and alkali uptake by the corn kernels. Improper drying and handling of corn causes fissuring and breakage, which causes overcooking. Soft kernels, broken kernels, or kernels with fissures take up water and alkali more quickly and cook faster. Thus, some kernels are overcooked and may dissolve during handling, which increases dry matter losses, and produces masa with poor properties.

A properly cooked corn kernel consists of enough gelatinized, swollen starch granules and hydrated protein matrix to produce a dough when it is stone-ground. The attrition of the stone disrupts the swollen starch granules and hydrated protein and causes dough formation. The amylose, amylopectin, and protein form a continuous system, i.e., "glue" that holds the ungelatinized starch and intact endosperm cells together in a cohesive dough. Overcooked corn often forms masa with a sticky consistency because too much glue is formed. The complex interaction between amylose, amylopectin, proteins, ungelatinized starch granules, and endosperm particles is not understood. More information on this complex could lead to many practical applications.

SUMMARY OF THE INVENTION

The invention described herein relates to novel white corn hybrids specifically selected for wet milling, and includes novel white corn hybrids that provide enhanced compositional characteristics and increased yields of critical components useful for novel end-product uses, and potential for reduced processing waste by-products in the wet milling process.

The present invention includes hybrid varieties of white corn having novel wet milling processing characteristics and novel feed value. The hybrids disclosed herein include the preferred embodiments of white corn having enhanced compositional characteristics, for example 1851W and E8272, and are of the genus species Zea mays L. These hybrids are bred and selected to yield improved and/or enhanced levels of one or more grain components, and to be effectively and efficiently wet milled.

The present invention further includes selecting hybrid varieties of white corn for wet milling based on particular grain components, for example, protein characteristic of the endosperm, an amino acid characteristic, a β-carotene characteristic, a xanthophyll characteristic, a starch characteristic, and combinations thereof.

The invention further includes an improved wet milling process, whereby the hybrids of the invention are easily separated into their components using an improved wet milling process that potentially increases plant efficiency in terms of quantity of product run verses time of operation.

The hybrids of the invention are further developed to yield elevated levels of one or more amino acids, for example, proline, pursuant to processing.

The invention also includes obtaining an essentially pure, very white, natural starch having improved functional properties that does not require chemical modification to achieve such whiteness. The invention includes selecting white corn hybrids that yield in the wet milling process a high protein, nearly carotene-free gluten meal.

The invention further includes an improved method of wet milling in order to extract and separate the grain components of white corn hybrids.

The invention further includes the identification of a unique starch complex that significantly effects steep time, cook time, cook temperature, and waste reduction in the alkaline cooking process of tortillas.

The invention further includes the development of a model for tortilla production that can be used as a screening tool by plant breeders.

Other features and advantages of the present invention will become apparent from the following detailed description.

DEFINITIONS

The following definitions are helpful in understanding the specification and claims. The definitions provided herein should be borne in mind when these terms are used in the following examples and throughout the instant application.

ADVANTAGE is the advantage a hybrid has compared to another hybrid for yield (bushels per acre), moisture content, income, population, stand, roots, and test weight.

ALEURONE COLOR is the color of the aleurone scored as white, pink, tan, brown, bronze, red, purple, pale purple, colorless or variegated.

AMYLOPECTIN STARCH averages about 70–75% of the total corn starch derived from yellow corn seed and is a branch molecule with alpha-(1,6) linked branch points and linear regions of alpha-(1,4) linked glucose units.

AMYLOSE STARCH averages about 25–30% of the total corn starch, and is an essentially linear molecule of glucose units linked together.

BUSHELS PER ACRE (BU ACR) is the actual yield of the grain at harvest adjusted to 15.5% moisture. ABS is in absolute terms and % MN is percent of the mean for the experiments in which the hybrid was grown.

COB COLOR is the color of the cob, scored as white, pink, red or brown.

COMMON RUST (*Puccinia sorghi*) is a 1 to 9 visual rating indicating the resistance to Common Rust. A higher score indicates a higher resistance.

CORN PLANT PARTS means cells, protoplasts, tissue cultures from which corn plants can be regenerated, calli, plant clumps, embryos, pollen, flowers, kernels, ears, cobs, leaves, husks, stalks, roots, root tips, anthers, silk and other intact organs or tissues of a corn plant.

CROWN RATING: 1–8 (8=very small crown).

DENT RATING: 1–8 (8=no dent).

DIFFERENTIAL SCANNING CALORIMETER allows the direct measurement of the energy required to gelatinize starch.

DRYDOWN (D/D) is a relative rate at which a hybrid will reach acceptable harvest moisture compared to other hybrids on a 1–9 rating scale. A low score indicates a hybrid that dries relatively fast while a high score indicates a hybrid that dries slowly.

DROUGHT TOLERANCE (D/T) refers to a 1–9 rating for drought tolerance and is based on data obtained under stress conditions. A low score indicates good drought tolerance and a high score indicates poor drought tolerance.

EAR HEIGHT (EAR HT) refers to ear height as measured from the ground to the top developed ear node attachment and is measured in inches.

EAR HEIGHT RATING (E/HT/R) is a 1–9 rating with a 1, 5 and 9 representing a very low, average and very high ear placement, respectively.

EAR FLEX refers to ear size in response to plant populations. A determinate ear size means that the ear length remains fairly constant over a wide population range. A flex ear will change in length or girth in response to different plant populations.

EAR TYPE refers to the ability of the ear to flex and is classified as Fixed (determinate ear size), Flex (indeterminate ear size), or Semi-Flex.

EMERGENCE is the rating of growth to the $2^{nd}$ collared leaf (V2) stage, 1=excellent.

ENDOSPERM COLOR is the color of the endosperm scored as white, pale yellow or yellow.

ENDOSPERM TYPE is the type of endosperm scored as normal, way or opaque.

GDD is the number of growing degree days or heat units required for an inbred line or hybrid to reach anthesis or pollen shed from the time of planting. For each hybrid, it takes a certain number of GDDs to reach various stages of plant development. GDDs are a way of measuring plant maturity.

GDU=Growing Degree Unit.

GDU TO PHYSIOLOGICAL MATURITY is the number of growing degree units required for an inbred or hybrid line to have approximately 50% of plants at physiological maturity from time of planting.

GDU TO POLLEN is the number of growing degree units required for an inbred or hybrid line to have approximately 50% pollen shed from the time of planting.

GDU TO SILK is the number of growing degree units required for an inbred line or hybrid to have approximately 50% of the plants with silk emergence from time of planting.

GRAIN comprises mature corn kernels produced by commercial growers for purposes other than growing or reproducing other species.

GRAIN COLOR is the color of the grain scored as white, yellow, orange, red, purple or brown. Color differences may be due to genetic differences in pericarp, aleurone, germ, and endosperm.

GRAY LEAF SPOT (*Cercospora zeae*) disease rating is scored visually on a scale of 1 to 9, with 9 indicating the highest disease resistance.

HARD/HORNEOUS ENDOSPERM (%): visual evaluation according to guidelines developed by Quaker Oats.

HIGH PERFORMANCE SIZE EXCLUSION CHROMATOGRAPHY (HPSEC) of starch allows for the determination of degree depolymerization (from shear, enzymes or other causes) during processing of starch and starch-based ingredients or foods.

HYBRID refers to the progeny of a cross fertilization between parents belonging to different genotypes, or the first generation offspring of a cross between two homozygous individuals differing in one or more genes.

KERNEL is the corn caryopsis comprising a mature embryo and endosperm which are products of double fertilization.

KERNEL DENSITY is determined by pre-weighing 100 kernels and placing them in a Micromeritics helium-air comparison pycnometer which measures volume in cubic centimeters. Kernel density is calculated as mass of the 100 kernels divided by their volume.

KERNEL ROWS is the average total number of kernel rows on the ear. If the rows are indistinct, this value is the average number of kernels located around the circumference of the ear at the mid-point of its length.

LATE SEASON INTACTNESS: ability to maintain plant integrity or intactness prior to harvest, 1=excellent.

MASA is the corn-based dough used inproducing corn chips and corn-based tortillas and tortilla chips.

MATURITY TO SILK is the maturity time from planting to 50% of plants in silk and is measured in days and heat units.

MATURITY TO POLLEN is the maturity time from planting to 50% of plants in pollen and is measured in days and heat units.

NIXTAMALIZATION is the process of taking dry corn and lime and combining them in a kettle with water that is heated to near boiling temperatures.

NORTHERN LEAF BLIGHT (*Exserohilum turcicum*) disease rating is scored visually on a scale of 1 to 9, with 9 indicating the highest disease resistance.

NUMBER OF EARS is the average number of ears per plant.

OIL (%) is the amount of the kernel that is oil, expressed as a percentage on a dry weight basis.

PERICARP COLOR is the color of the pericarp scored as colorless, orange, cherry red, red-purple, purple or brown.

PLANT COLOR is the color of the plant scored as very light green, moderate green or very dark green.

PLANT HEIGHT is measured from the ground to the tip of the tassel, and is measured in inches.

PROTEIN (%) is the amount of the kernel that is crude protein, expressed as a percentage on a dry weight basis.

RAPID VISCO-ANALYZER (RVA) is a means to measure the change in viscosity of starch under low shear rates when the temperature is increased to 95 degrees C.

RELATIVE MATURITY is a maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

RESPONSE TO LOW DENSITY: ability of a hybrid to respond to plant populations below 25,000 plants/acre, 1=excellent.

RESPONSE TO HIGH DENSITY: ability of a hybrid to respond to plant populations ranging from 25,000 to 30,000 plants/acre, 1=excellent.

ROOT STRENGTH refer to a 1–9 rating measurement of the ability of a plant to resist lodging or leaning more than 45 degrees, where 1, 5 and 9 represent outstanding, good and poor, respectively.

SEED refers to mature corn kernels produced for the purpose of propagating the species.

SEEDLING GROWTH: rating of growth from V2–V5 stage, 1=excellent.

SHANK LENGTH refers to a measurement rating of the length of the ear shank usually classified as short, medium, or long.

SOUTHERN LEAF BLIGHT (*Bipolar maydis*) disease rating is scored visually on a scale of 1 to 9, with 9 indicating the highest disease resistance.

STALK STRENGTH refers to a 1–9 measurement rating of the ability of the plant to resist stalk breakage below the node where the ear is attached, where 1, 5 and 9 represent outstanding, good and poor, respectively.

STARCH (%) is the amount of the kernel that is starch, expressed as a percentage on a dry weight basis.

STARCH BLEEDING (%): percent of kernels demonstrating starch bleeding around the embryo.

STAYGREEN is the ability of the plant to maintain photosynthesis in the leaves and stalks through drydown, 1=excellent.

STEWART'S WILT (swilt; *Erwinia stewartii*) disease rating is scored visually on a scale of 1 to 9, with 9 indicating the highest disease resistance.

THINS (%): percent of kernels passing through a 20/64" round hole screen.

100 KERNEL WEIGHT is a weight measurement of 100 randomly selected kernels that is averaged to estimate relative kernel size.

Unless otherwise defined, all technical and scientific terms used herein have the same meaning as commonly understood by on of ordinary skill in the art to which this invention belongs. Although methods and materials similar or equivalent to those described herein can be used to practice the invention, suitable methods and material are described below. All publications, patent application, patents, and other references mentioned herein are incorporated by reference in their entirety. In case of conflict, the present specification, including definitions, will control. In addition, the materials, methods and example are illustrative only and not intended to be limiting.

DETAILED DESCRIPTION OF THE PREFERRED EMBODIMENTS

It is to be understood that both the foregoing general description and the following detailed description are exemplary and explanatory only and are not restrictive of the invention as claimed.

A small quantity of white corn has traditionally been wet milled with difficulty to produce specialty products with very bright whiteness. To be economically feasible, the value of the resultant specialty starch has yet to overcome the production premiums of time and expense as white corn is known not to wet mill efficiently. Contrary to expectations, the white corn hybrids of the instant invention may be effectively and efficiently wet milled, and in fact, perform superiorly to yellow dent corn with standard wet milling techniques. That is, the components of the white corn hybrids are easily separated with standard wet milling techniques, and may also be processed more efficiently with improved wet milling techniques.

A representative embodiment of the instant invention includes Wilson Genetics white corn hybrids 1851W and E8272 showing consistent kernel characteristics and grain component yields subject to wet milling. These preferred hybrids further exhibit superior quality components, and are particularly well-suited for novel methods of wet milling.

Wilson Genetics hybrids 1851W and E8272 are single cross hybrids that are related by a common female parent. Both hybrids have a male parent that was derived from tropical germplasm. A comparison of their traits are summarized as follows:

TABLE 1

EXEMPLARY HYBRID DESCRIPTION INFORMATION FOR HYBRIDS 1851W and E8272

| Traits | 1851W | E8272 |
| --- | --- | --- |
| Female Parent | WEBF428C | WEBF428C |
| Male Parent | WICY226C | WICY418C |
| Relative Maturity (Days) | 116–118 | 115–117 |
| GDU to Silk | 1499–1538 | 1499–1538 |
| GDU to Pollen | 1499–1538 | 1499–1538 |
| GDU to Physiological Maturity | 3175–3198 | 3150–3198 |
| Plant Characteristics: | | |
| Plant Height (inches) | 100–104 | 98–102 |
| Ear Height (inches) | 50–56 | 50–56 |
| Shank Length | Medium | Medium |
| Kernel Rows | 16 | 14–16 |
| Plant Color | Dark Green | Dark Green |
| Grain Color | White | White |

TABLE 1-continued

EXEMPLARY HYBRID DESCRIPTION INFORMATION FOR HYBRIDS 1851W and E8272

| Traits | 1851W | E8272 |
| --- | --- | --- |
| Cob Color | White | White |
| Ear Type | Long, Girthy | Long, Slender |
| Ear Flex | Excellent (2.0) | Excellent (2.0) |
| Number of Ears/Stalk | 1 | 1 |
| Emergence | Very Good (3.0) | Very Good (3.0) |
| Seedling Growth | Very Good (4.0) | Very Good (3.0) |
| Late Season Intactness | Excellent (2.0) | Good (5.0) |
| Staygreen | Excellent (2.0) | Very Good (4.0) |
| Drydown | Good (5.0) | Very Good (4.0) |
| Stalk Strength | Excellent (2.0) | Very Good (4.0) |
| Root Strength | Good (5.0) | Good (5.0) |
| Drought Tolerance | Excellent (2.0) | Excellent (2.0) |
| Response to Low Population | Excellent (2.0) | Excellent (2.0) |
| Response to High Population | Very Good (3.0) | Very Good (4.0) |
| Grain Charcateristics | | |
| Pericarp Color | White | White |
| Aleurone Color | White | White |
| Endosperm Color | White | White |
| Endosperm Type | Hard | Hard |
| Horneous Endosperm (%) | 85–90 | 85–90 |
| 100 Kernel Wt. (grams) - unsized | 38.3–41.0 | 34.0–38.0 |
| Protein (%) - dry weight basis | 9.0–11.0 | 9.0–10.0 |
| Oil (%) - dry weight basis | 4.2–4.9 | 3.8–4.4 |
| Kernel Density (g/cc) | 1.31–1.34 | 1.30–1.31 |
| Thins (% thru a 20/64" screen) | 5.0–10.0 | 10.0–15.0 |
| Crown Rating | 6.5 | 6.0 |
| Dent Rating | 7.0 | 6.5 |
| Disease Resistance | | |
| Northern Leaf Blight | Excellent (1.0) | Excellent (1.0) |
| Southern Corn Leaf Blight | Excellent (2.0) | Excellent (2.0) |
| Gray Leaf Spot | Excellent (1.0) | Excellent (1.0) |
| Common Rust | Average (6.0) | Very Good (3.0) |
| Steward's Bacterial Wilt | Excellent (2.0) | Average (6.0) |

This invention includes hybrid white corn seeds, including those of 1851W and E8272, the hybrid corn plants produced from the hybrid corn seeds, and variants, mutants and modifications of 1851W and/or E8272 and similarly classified and characterized hybrids. This invention may also relate to the use of such hybrids in producing other hybrids, e.g., three-way or double cross hybrids. The terms variant, trivial modification and mutant refer to a hybrid seed where a plant produced by that hybrid seed is phenotypically similar to, for example, the 1851W and E8272 hybrids. As used herein, the term "plant" includes plant cells, plant protoplast, plant cell or tissue culture from which a corn plant can be regenerated, plant calli, plant clumps and plant cells that are intact in plants or parts of plants, such as flowers, kernels, ears, cobs, leaves, husks, stalks and the like.

The inbred parents of the illustrative hybrid 1851W include a tropical, and preferably, male parent WICY226C, and a domestic, and preferably, female parent WEBF428C. The inbred parents of the illustrative hybrid E8272 include a tropical, and preferably, male parent WICY418C, and a domestic, and preferably, female parent WEBF428C. The tropical inbred parents are selected for grain characteristics such as hardness, disease resistance and diversity, but show good yield when crossed with U.S. derived stiff stalks. As used herein, the term "tropical" refers to germplasm originally collected from regions outside of the United States. The hybrids are selected from various inbred crosses based upon one or more grain characteristics, e.g., color (bright white), yield, kernel hardness, cap smoothness, kernel size and shape uniformity, the protein characteristics of the endosperm, the character of the starch, combinations of these and the like.

The inbred parents as well as the exemplary $F_1$ hybrid crosses resulting therefrom disclosed herein have been deposited in accordance with MPEP § 608.01(p) and 37 C.F.R. §§ 1.801–1.809, with the American Type Culture Collection, 10801 University Blvd., Manassass, Va., 20110–2209 and assigned ATCC accession numbers: PTA-2921 for WICY226C; PTA-2924 for WEBF428C; PTA-2923 for 1851W; PTA-2925 for WICY418C; and, PTA-2922 for E8272.

Contrary to the expectation that white corn performs poorly, if at all, in wet milling applications, the instant hybrids exhibit superior performance with standard wet milling methods, and potentially, as well with the novel methodology disclosed herein. More specifically, the grain components of the instant hybrids (starch, fiber, protein, and embryo) separate cleaner and easier than other white corn, and as well as many varieties of yellow dent corn, resulting in purer extracted products and higher milling capacity.

The instant invention provides novel corn gluten meal, novel feed ingredient use of the corn gluten meal, novel starch, and use of white corn to advantage in the wet milling process, not previously known. Extraction of corn gluten meal and starch from corn plants is well known and typically involves a wet milling process. In accordance with the present invention, a wet milling process is used to advantage to extract the corn starch and protein from the corn kernels. The extracted starch is processed as described infra; the protein extracted is processed in manners consistent with those which are well known in the art. Conventional wet milling is comprised of the steps of steeping, grinding the corn kernel and separating the components of the kernel. Prior to steeping, the kernels are subjected to a cleaning process to remove any debris that may be present. This cleaning process is usually performed at the wet milling plant. The kernels are then steeped in a steep tank where they are contacted with a countercurrent flow of water at an elevated temperature, approximately 120° F., the water containing sulfur dioxide at a concentration of approximately 0.2% by weight. The kernels remain in the steep tank for approximately 24–48 hours. The kernels are then dewatered and subjected to various sets of attrition type mills.

In wet milling processes, a first set of attrition type mills generally grind and rupture the kernels releasing the germ from the kernel. A commercial attrition type mill suitable for the wet milling is available under the brand name Bauer. (Andritz Incorporated, Muncy, Pa.). Centrifugation separates the released germ from the rest of the kernel. A typical commercial centrifugation separator is the Merco Centrifugal Separator. (Alpha Laval Separations, Inc., Warminisder, Pa.). Throughout the grinding steps, the kernel and the kernel components are maintained in a slurry of approximately 40% by weight solids.

Next, the remaining kernel components, including the starch, hull, fiber, and gluten, are subjected to another set of attrition mills to further grind the components and separate the hull and fiber from the starch and gluten, and then passed through a set of wash screens to separate the fiber components from the starch and gluten. The starch and gluten pass through the screens. The fiber component does not pass through. Centrifugation, or alternatively, a third grind followed by centrifugation, is used to separate the starch from the protein. Centrifugation produces a starch granule containing slurry that is dewatered, washed with fresh water and dried to approximately 12% moisture. The substantially pure starch of the present invention is extracted from the white corn grain in the above-described manner.

Typical yields of starch and gluten from the processes disclosed herein with yellow dent corn grain fall within the range of 65–67% d.b. and 4.6–5% d.b. for starch and gluten, respectively. The amounts obtained from the process of milling the hybrids of the instant invention are approximately 70% d.b. and 6–7% d.b., respectively, demonstrating that the wet milling of the instant hybrids results in higher yield of starch and gluten. The gluten recovered from wet milling with respect to the present invention contains significantly more protein (77–82%) than gluten recovered from yellow dent corn (60–66%). Furthermore, analysis of the gluten fraction recovered from wet milling demonstrates that gluten from yellow dent corn contains 22–23% starch, while the gluten from the present invention contains less than 9% starch, clearly indicating a distinct improvement in the protein, starch separation with the present invention; that starch having percentages of amylose and amylopectin ranging from 11–17% and 80–86%, respectively. Moreover, overall milling efficiency, compared to yellow dent, is improved in processing the hybrids of the instant invention based upon a combination of increased speed of separation of protein and starch, improved starch and gluten yields and potentially less chemical usage Preferably, to preserve the desirable characteristics of end products resulting from the present invention wet milling of selected hybrids of the invention are carried out on an identity preserved basis. As used herein, "identity preserved basis" means that at least about 70%, preferably at least 90%, and more preferably at least 99%, of the white corn that is milled in a milling run is derived from a single hybrid of the present invention. That is, a novel processing methodology preserves special characteristics based upon the absence of grain commingling during milling. Hence, the hybrid maintains its identity from the time of planting through harvesting, storage, and delivery to the processing plant. Preferably, the minimum purity standard that is used is 98%. Heretofore, commingling of grain has been a predominant wet milling methodology employed in the industry, effectively "averaging" the advantages and disadvantages of myriad corn varieties.

White corn hybrids of the present invention may be selected for wet milling based upon one or more selection criteria by which these hybrids may be identified and used to provide the advantages discussed herein. In particular, these selection criteria may include: gluten and starch yields; quality and/or level of endosperm protein; protein solubility; levels of xanthophyll (preferably the substantial lack thereof); levels of β-carotene (preferably the substantial lack thereof); protein digestibility; and amino acid characteristics (e.g., increased proline content). By way of further example, additional hybrid selection criteria may include unique characteristics of their starch component, such as, viscosity, retrogradation and thermal peaks.

The 1851W hybrid is exemplary with respect to these selection criteria. Some of the specific advantages of the 1851W hybrid include, e.g., lower starch levels in gluten, elevated amino acid levels, increased protein yield derived from hard endosperm, reduced pigmentation component levels and increased solubility. Corn gluten components are generally comprised of 20–23% starch, while the gluten of these hybrids contains less than 9% starch. A higher level of selected desirable amino acids is found within the approximately 80% protein yield. For example, in addition to a detectably elevated proline level in 1851W, the levels of xanthophyll and β-carotene are extremely low. The solubility of proteins in water is increased 6-fold; the elevated solubility of fiber and protein (72% versus 30–35%) enhances the digestibility. The increased digestibility is attributable to the increased protein level, rather than the insoluble complex components (hemocellulose) of the cell wall. The starch of the 1851W hybrid also resists gelatinization. The improved starch of the hybrids disclosed herein is natural but carries characteristics of a modified starch as discussed infra. The unique property of the 1851W starch includes its ability to remain viscous and resist gelling longer than other corn varieties. This is advantageous in the food industry.

The E8272 hybrid is similar to 1851W with respect to the selection criteria for wet milling products and co-products. Some of the specific advantages of the E8272 hybrid include, e.g., bright white grain and endosperm color, uniform kernel size, above average protein and oil, low ash content, excellent density, and low levels of xanthophyll and beta-carotene.

The starch obtained from the hybrids of the instant invention generally also possess advantages over the starch obtained from typical yellow dent corn. Typically, yellow cornstarch from wet milling is subject to any one or more of eight general treatments to make it suitable for a variety of end-uses. These treatments include, for example, bleaching, thin boiling, acid treatment, enzyme treatment, dextrinization or dryroasting, etherification, esterification, and crosslinking. Starches treated by one or more of these treatments are commonly referred to as chemically modified starch. Bleaching (or oxidation) lightens the color of the starch granules and is normally necessary to make corn starch suitable for use in laundry starch, paper coating, textile size and as a food ingredient, but tends to reduce the viscosity of the starch paste produced therefrom.

In contrast, the pure white starch of the present invention requires no bleaching thus saving the wet miller the cost of this normally required modification process. Further, the preservation of the viscosity, normally lost by the bleaching process, increases the water holding capacity of the starch of the present invention, thereby providing crosslinking sites to produce stabilized starches resistant to acid and shear, useful in adhesives and coatings, and may be useful in protein interactions in food and pharmaceuticals. This unique starch, due to its enhanced crosslinking, is useful for wastewater treatment and metal recovery based upon its enhanced electrolyte binding capability. Moreover, this starch has enhanced capability of providing sites for attachment of other polymers, thus, eliminating one step in producing amphoteric starch. The present invention has significant advantage for use in the food ingredient business. This starch is naturally occurring in this variety, eliminating the need for chemical modification and minimizing FDA regulatory approval.

Starches are often modified by numerous techniques known in the industry to change the behavioral characteristics of the starch, yet still essentially retain the caloric value of the native or unmodified starch. One type of modification is crosslinking. When an aqueous dispersion of native starch is heated, the starch granules begin to swell, and the dispersion develops a short, salve-like texture that is essential in imparting palatability and in thickening food systems. However, during the process of cooking the native starch, this textural state rapidly changes to an elastic, rubbery state when the swollen granules rupture. Minor variations in cooking time, temperature and concentration as well as shear and pH are sufficient to effect this transformation. Crosslinking modifications act to strengthen the granules by reinforcing the hydrogen bonds that are responsible for holding the granules intact and these are used to overcome the extreme sensitivity of the swollen starch granules to handling and processing conditions.

Aqueous dispersions of crosslinked starch are often used under conditions involving prolonged storage at relatively low temperatures and/or exposure, at times, to repeated freezing and thawing cycles. Under such circumstances involving exposure to low temperature, there is a distinct loss in the hydrating power of the starch that is present in food products, thereby resulting in syneresis, an exudation of liquid, together with a marked deterioration in the texture, color and clarity of the product. Attempts to overcome these difficulties have involved the introduction of substituted branches onto the starch molecule by means of various chemical derivatization reactions, for example, reacting the starch with a monofunctional reagent to introduce substituent such as hydroxypropyl, phosphate, acetate or succinate groups. Such substituents stabilize the starch by interfering with the association between molecules or portions of the same molecule, thus reducing the tendency of the substituted starches to lose their hydration ability and clarity upon storage, particularly at low temperatures. These derivatization reactions may be carried out alone, but are frequently employed in combination with crosslinking.

Alkali Cooking Basics

Masa is the corn-based dough that forms the base for corn chips, corn-based tortillas, and tortilla chips. Alkali processors produce masa by cooking corn in the presence of lime (calcium oxide) in a process known as "nixtamalization."

Nixtamalization begins by combining dry corn and lime in a kettle of water and cooking the mass with steam injection to near boiling. Depending on the product being made, the cooking time will vary. Tortilla chips require between 5 and 10 minutes of cooking, while corn chips require 20 to 30 minutes. Even longer cooking times are necessary for tortillas.

Some processors stop the cooking process by quenching the corn with cold water. Others simply drain the corn. Either way, the corn next must steep in tanks for 8 to 12 hours. Because the cooking step typically only partially cooks the kernels, steeping is necessary to allow moisture and lime to be distributed evenly.

After steeping, the corn is ground to form masa. Next, the masa is formed and fried to make corn chips; formed and baked to create tortillas; or formed, baked, cut and fried for tortilla chips.

Several variables affect the results of nixtamalization including corn hardness, lime concentration, cooking time and temperature, steep time and temperature, degree of cooking, and the final moisture content. Although nixtamalization has a long history, recreating the process on an industrial scale presents several challenges.

First, heating huge tanks of water and corn for cooking requires a great deal of energy. The steep time also is very critical. If the steep is too short, the kernels will have hard areas that are difficult to grind. The resulting masa also may tend to be dry and crumbly. Steeping for too long yields a sticky masa that is difficult to sheet for further processing.

Another challenge is that the cooking-steeping part of creating masa-based products is done batchwise, while the remainder is continuous. If something goes wrong with cooking or steeping, the rest of the line will experience costly downtime. If a mechanical breakdown occurs on the continuous part of the process, the time-sensitive cooking and steeping processes may generate waste while the problem is corrected.

From cooking to forming and finishing corn-based products, dry matter loss (DML) is an ongoing battle. In fact, some manufacturers experience dry matter losses as high as 8% to 17%. Even the most diligent of companies may experience yield-robbing DMLs because the corn itself can be a contributing factor.

EXAMPLE 1

This example illustrates the extraction of the substantially pure starch of the present invention from white corn hybrid line 1851W and analyzes the individual components to determine various characteristics. The extraction and analysis of the starch, gluten and fiber components from the present invention (1851W) is summarized in Table 2. Also included in Table 2 is a comparison of the grain analysis of the present invention (1851W) to that of yellow dent corn. The improved variety of the corn of the instant invention, an $F_1$ hybrid, produces grain with higher protein, and extremely low levels of carotenoids. It is also important to note that the 1851W gluten and fiber components have substantially higher protein levels than the yellow corn. In addition, the fiber portion of 1851W has significantly higher protein solubility values than the yellow corn. The extraction process is outlined in a flow diagram in FIG. 1. Analysis of the components presented in Table 2 were completed according to standard procedures used by the Experiment Station Chemical Laboratories, University of Missouri-Columbia, Columbia, Mo., in accordance with AOAC standards.

Illustrative yield comparisons of the hybrids, as expressed in potential added value of grain components, are summarized and compared, in Table 3 below, to yellow dent corn.

TABLE 3

Potential Added Value Yield Comparison

| VARIETY | Component | Yield (milling) | $/# | $/bushel | Added value ($/bushel) |
|---|---|---|---|---|---|
| Yellow dent | Starch | 67% | 0.08 | 2.58 | — |
| | Gluten | 2.2#/BU | 0.12 | | — |
| | Fiber | 9#/BU | * | * | — |
| | Embryo | 5.3#/BU | 0.20 | 0.49 | — |
| | Steep water | | 0.20 | | — |
| | Amino acid (proline) | — | 40.00/oz. | — | — |
| 1851W | Starch | 70.2% | 0.11 | 3.71 | +1.13 |
| | Gluten | 3#/BU | | | +0.73 |
| | Fiber | 8#/BU | * | * | +0.32 |
| | Embryo | 5.3#/BU | 0.20 | 0.54 | +0.05 |
| | Steep water | | 0.20 | | +0.40 |
| | Amino acid (proline) | 3.2 oz./BU | 40.00/oz. | — | +127.00 |

As shown above, 1851W grain (Colorado Sweet Gold variety) had a starch milling yield of 70.2%, i.e., 33.7 pounds from each 56 pound bushel at 15% moisture, while

TABLE 2

Wet Milling Comparison of 1851W vs. Standard Yellow Hybrid

| Trait | 1851W Gluten | Yellow Corn Gluten | 1851W Fiber | Yellow Corn Fiber | 1851W Starch | Yellow Corn Starch | 1851W Grain | 1664 Grain |
|---|---|---|---|---|---|---|---|---|
| Crude Protein (%)* | 77.46 | 71.90 | 19.3 | 10.40 | 0.31 | 0.26 | 9.86 | 8.81 |
| Crude Fat (%)* | 1.04 | 1.38 | 1.91 | 47.12 | 0.00 | 0.08 | 4.49 | 4.21 |
| Crude Fiber (%)* | 0.68 | 0.85 | 7.62 | 6.04 | 0.07 | 0.27 | 2.34 | 2.05 |
| Ash (%)* | 2.22 | 3.35 | 5.40 | 0.87 | 0.09 | 0.21 | 1.26 | 1.45 |
| ADF (%)* | 2.30 | 0.96 | 10.01 | 22.43 | 0.06 | 0.02 | 3.64 | 2.90 |
| NDF (%)* | 2.82 | 1.65 | 44.94 | 39.39 | 0.43 | 0.31 | 13.24 | 11.35 |
| Cellulose (%)* | 2.15 | 1.93 | 9.45 | 17.47 | 0.03 | 0.06 | 2.73 | 2.65 |
| Phosphorus (%)* | 0.58 | 0.91 | 0.99 | 0.24 | <0.06 | <0.05 | 0.26 | 0.31 |
| Starch (%)* | 9.93 | 10.53 | 28.93 | 10.41 | 96.28 | 98.25 | 64.67 | 71.73 |
| Protein Solubility (%)* | 9.25 | 8.22 | 6.84 | 1.22 | <0.40 | <0.4 | 0.95 | <0.40 |
| Beta Carotene (ug/100 g) | 104.00 | 345.0 | 202.00 | 91.0 | <0.05 | <0.05 | <0.05 | 107.5 |
| Xanthophyll (ug/100 g) | 50.20 | 1804.0 | 89.70 | 0.22 | <0.08 | <0.08 | <0.08 | 4.08 |
| Fatty Acids (% of total fat): | | | | | | | | |
| Myristic (14:0) | 0.00 | 0.00 | 0.09 | 0.03 | 0.00 | 0.00 | 0.03 | 0.00 |
| Myristoleic (14:1) | 0.00 | 0.00 | 0.00 | 0.00 | 0.00 | 0.00 | 0.00 | 0.00 |
| Palmitic (16:1) | 11.98 | 14.17 | 13.66 | 10.14 | 27.87 | 27.39 | 11.68 | 13.14 |
| Palmitoleic (16:1) | 0.27 | 0.18 | 0.00 | 0.09 | 0.00 | 0.00 | 0.13 | 0.12 |
| (17:0) | 0.00 | 0.00 | 0.00 | 0.00 | 0.00 | 0.00 | 0.00 | 0.00 |
| Stearic (18.0) | 2.16 | 1.86 | 2.35 | 1.91 | 2.63 | 2.36 | 1.93 | 1.94 |
| Oleic (18:1) | 21.29 | 21.81 | 22.51 | 26.71 | 10.84 | 12.06 | 22.43 | 23.77 |
| Linoleic (18:2) | 57.80 | 55.02 | 57.45 | 58.04 | 44.81 | 42.41 | 59.42 | 56.42 |
| Linolenic (18:3) | 2.44 | 2.60 | 2.99 | 0.89 | 2.11 | 2.86 | 1.06 | 1.80 |
| (w18:4) | 0.00 | 0.00 | 0.00 | 0.00 | 0.00 | 0.00 | 0.00 | 0.00 |
| Arachidic (20:0) | 0.35 | 0.35 | 0.37 | 0.55 | 0.00 | 0.00 | 0.46 | 0.45 |
| Arachidonic (20:4) | 0.00 | 0.00 | 0.00 | 0.00 | 0.00 | 0.00 | 0.00 | 0.00 |
| (w20:5) | 0.00 | 0.00 | 0.00 | 0.00 | 0.00 | 0.00 | 0.00 | 0.00 |
| Docosanoic (22:0) | 0.35 | 0.25 | 0.26 | 0.29 | 0.00 | 0.00 | 0.27 | 0.27 |
| Erucic (22:1) | 0.00 | 0.00 | 0.00 | 0.00 | 0.00 | 0.00 | 0.00 | 0.00 |
| (w22:6) | 0.00 | 0.00 | 0.00 | 0.00 | 0.00 | 0.00 | 0.00 | 0.00 |
| Lignoceric (24:0) | 0.25 | 0.23 | 0.14 | 0.21 | 0.00 | 0.00 | 0.20 | 0.19 |
| (w24:1) | 0.00 | 0.00 | 0.00 | 0.00 | 0.00 | 0.00 | 0.00 | 0.00 |

Values are based on a 0% moisture basis yellow dent corn yielded 67% starch (~32.2 pounds per bushel). By way of example, food grade starch, at the time of this application, is worth $0.08 per pound. 1851W starch does not require bleaching for certain applications and was sold at $0.11 per pound (33.7#×$0.11=$3.71 per bushel for the hybrid). Yellow dent selling at $0.08 per pound×32.2 pounds=$2.58 per bushel. The resultant added value in the hybrid is $1.13 per bushel. Additionally, the hybrid exhibits various unique properties as described herein. Processing applications wherein chemical modification of the starch is not required result in higher added value. For example, a $0.16 per pound savings for 33.7 pounds per bushel results in a $5.39 per bushel added value.

The gluten yielded by the hybrid was 3 pounds per bushel at 80% protein (dry-matter basis) as compared to 2.2 pounds per bushel at 60% protein for yellow dent corn. The hybrid gluten is essentially 100% digestible, whereas the yellow dent corn is only 48% digestible. Hence, 3 pounds per bushel @ 80%=2.4 pounds×100% digestibility=2.4 pounds available protein per bushel of hybrid corn versus 0.64 pounds for yellow dent (2.2 pounds per bushel @ 60%=1.32 pounds per bushel×48% digestibility=0.64 pounds available protein per bushel). If, for instance, yellow dent derived gluten is worth $0.12 per pound, then the 0.64 pounds of available protein per bushel is worth $0.4125 per pound. There is an additional 1.76 pounds of protein available in the 1851W hybrid example, resulting in a $0.73 per bushel added value.

With regard to fiber, yellow dent corn yields 9 pounds per bushel comprised of 23% starch and 10% protein, and is 38% soluble. The hybrid example disclosed in Table 3 yields only 8 pounds of fiber per bushel. However, the composition of that fiber is 8% starch and 20% protein, and the fiber component is 72% soluble. Lower starch values and higher protein and solubility values are considered positive results. Current values of fiber are unknown. However, it is reasonable to assume that adding 10% (protein) steep water to the fiber makes a 30% protein gluten feed product that is competitive with the standard 20% market product. By way of example, this product is similar to distillers dried grains ("DDG") in value. Estimating the worth at approximately $120.00 per ton versus $40.00 per ton (at 50% moisture) for the 20% gluten feed product adds value of $0.32 per bushel.

If the embryo fraction of the kernel is typically sold to oil extractors at a price of $180.00 per ton, and yellow dent corn yields 5.3 pounds per bushel at 46.5% oil, then, 2.46 pounds at $0.20 per pound is worth $0.49 per bushel. The 1851W hybrid yields 5.3 pounds per bushel at 51.2% oil. The result is 2.71 pounds, that is worth $0.54 per bushel, or $0.05 added value per bushel. Moreover, if the oil is extracted on-site and subsequently sold to refiners, the extracted oil product may be worth up to $0.49 per pound. Present extraction technologies allow 90–95% efficiency. Hence, the hybrid develops $1.19 value (2.71 pounds×90%×$0.49 per pound) as compared to yellow dent corn (2.46 pounds× 90%×$0.49), resulting in added value of $0.11 per bushel. Remaining is 2.8 pounds of meal that may be made into starter feeds or sold as regular gluten at $0.12 per pound for an additional added value of $0.34 per bushel.

Next, if steep water value is estimated at $0.20 per pound for soluble proteins (provided the $SO_2$ used in the steeping process can be neutralized) at 2 pounds per bushel, there is an added value of $0.40 per bushel.

Various amino acids that are used in both the food and pharma industries may be isolated from corn, provided they are presented in sufficient amounts. By way of example, if the worth of proline is estimated at approximately $40.00 per ounce, and the instant hybrids contain approximately 3.2 ounces per bushel, the added value of an additional $127.00 per bushel results.

As shown in Table 4, without excessive and/or repeated steeping and recycling during the wet milling process, the recovered gluten meal of the present invention, contains significantly more protein with increased digestibility, less phosphorus, less ash, and significantly less beta-carotene levels. The combination of these traits makes a novel feed ingredient that demands a higher value. Currently in the market place, there is an estimated increased value of this type of product ranging from $80.00–$150.00 per ton. Key market segments that could utilize this type of product includes feed operations where the absence of carotenoid pigments enhances the color of the flesh (trout) or the fat (swine, cattle), where the increased digestible protein lowers input costs, and for operations that are seeking alternative protein sources that are not animal derived.

TABLE 4

Gluten Meal Comparison

| TRAIT | YELLOW GLUTEN | 1851W GLUTEN |
| --- | --- | --- |
| Protein (%, db) | 68.55–73.57 | 73.31–77.46 |
| Crude Fat (%, db) | 0.87–3.06 | 0.69–1.47 |
| Ash (%) | 2.93–4.45 | 1.67–2.90 |
| Phosphorus (%) | 0.67–0.98 | 0.36–0.58 |
| Beta-carotene (ug/100 g) | 300.0–345.0 | 80.0–104.0 |
| Xanthophyll (mg/lb) | 130.0–170.0 | 5.0–25.0 |

EXAMPLE 2

This example compares the substantially similar characteristics of the hybrid E8272 with those previously described herein for the hybrid 1852W. The extraction techniques and comparative analysis are summarized below.

A 1.159 kg sample of E8272 and a 1.158 kg sample of 1851W were wet milled in a laboratory of the Center for Crops Utilization Research, Iowa State University (Ames, Iowa) to obtain high-quality corn starch, gluten meal, fiber and germ. The samples were steeped in 2.5 liters of solution containing 0.5% lactic acid and 0.2% $SO_2$ at 50° C. for 40 hours. The steeped corn was strained and the volume and pH of steep water measured. The steep water was then analyzed for dissolved solids.

The steeped corn was separated into several 200 gram fractions. Each fraction was ground with 200 ml water in a 1-liter Waring blender equipped with blunted blades and set at 50% speed for 4 minutes. The coarsely ground slurries were combined into a 4-liter bucket. One liter of water was added to the slurry. The slurry was mixed with a spatula and allowed to settle for 30 seconds, allowing the germ to float to the surface. The germ was skimmed off the surface with a 7-mesh hand-held skimming screen (pore size 2.8 mm) and placed into a 2-liter beaker. This procedure was repeated several times until essentially all free germ was removed. The germ was mixed with another liter of water and strained through a 16-mesh screen. The washed germ was then dried on the screen for 24 hours in a large-capacity forced-air oven set at 50° C. The underflow (wash water) generated from the 16-mesh screen was mixed with the degermed slurry.

The degermed slurry underwent fine grinding for 2 minutes in a 4-liter Waring commercial heavy-duty blender equipped with sharp blades and set at 90% speed. The finely ground slurry was then strained through a 7-mesh screen (pore size 2.8 mm) placed atop a 4-liter bucket. The coarse fiber fraction was scrapped off the screen using a spatula, mixed with 1 liter of water, and resifted through the 7-mesh screen. The coarse fiber fraction was then mixed a final time with another liter water and sifted once again through the 7-mesh screen. The coarse fiber fraction was placed into a large stainless steel pan. The remaining slurry was then strained through a 50-mesh screen (pore size 0.3 mm) placed atop another 4-liter bucket. The fiber was scraped off the screen using a spatula, mixed with 1 liter of water, and resifted through the 50-mesh screen. The fiber fraction was then mixed a final time with another liter of water and sifted once again through the 50-mesh screen. This fiber fraction was combined with the previously collected coarse fiber fraction and dried for 24 hours in a large-capacity forced-air oven set at 50° C.

The underflow (containing fine fiber and mill starch) was strained through a 200-mesh screen (pore size of 0.075 mm) placed atop a 4-liter bucket to separate the fine fiber fro the mill starch. The fine fiber was scraped off the screen using a spatula, mixed with the decant water, and resifted through the 200-mesh screen. The fine fiber was then mixed with another liter of water and sifted once again through the 200-mesh screen. The fine fiber was placed in a glass baking dish (separate from the coarse fiber) and dried for 24 hours in a large-capacity forced-air oven set at 50° C.

The remaining slurry (mill starch) was refrigerated at 4° C. and allowed to settle overnight for approximately 16 hours. After settling, approximately 4 liters of water were decanted from the mill starch slurry. The remaining slurry was mixed in a 10-liter glass bucket and adjusted to a specific gravity of 1.04. The adjusted slurry was then pumped at a rate of 300 ml/min onto a starch table (20' L×4" W) set at a 0.6 pitch. The gluten was collected in a 20-liter bucket placed at the distal end of the starch table, as the heavier starch settled onto the table. After the mill starch was exhausted, decant water was immediately pumped onto the table at the rate of 300 ml/min to rinse the starch fraction. The starch was allowed to settle for 10 minutes and another 3 liters of water were pumped onto the table at 300 ml/min to give the starch a final rinse. Simultaneously, an additional 500 milliliters of water were placed in a squeeze bottle and used to wash any remaining surface protein down the table. The starch was immediately scraped off the table and dried for 24 hours in a large-capacity forced-air oven set at 50° C. before storing.

The gluten slurry was centrifuged at 6000 rpm for 20 min. The decant water from the gluten slurry (rinse water) was tested for dissolved solids. The gluten solids were placed in a glass baking dish and dried in a large-capacity forced-air oven set at 50° C. for 24 hours.

Moisture content of solid fractions was determined in triplicate by drying 2 grams of the fraction in a convection oven at 130° C. for 3 hours according to AOAC standard methodology.

Dissolved solids in steep water was determined by drying the entire fraction in a large-capacity forced-air oven set at 50° C. for 24 hours followed by drying in a convection oven at 130° C. for 3 hours according to AOAC standard methodology. Dissolved solids in rinse water was determined by drying a 50 gram sample (in triplicate) in a large-capacity forced-air oven set at 50° C. for 24 hours followed by drying in a convection oven at 130° C. for 3 hours according to AOAC standard methodology.

An analytical comparison of the E8272 hybrid to the 1851W hybrid and standard yellow dent corn is presented in Table 5. Similarly to 1851W, E8272 shows higher protein levels and lower levels of carotenoids than standard yellow dent corn.

TABLE 5

Grain Comparisons of E8272 vs 1851W and Standard Yellow

| Trait | E8272 | 1851W | Standard Yellow |
|---|---|---|---|
| Crude Protein (%)* | 11.33 | 9.86 | 8.81 |
| Crude Fat (%)* | 5.01 | 4.49 | 4.21 |
| Crude Fiber (%) | 2.11 | 2.34 | 2.05 |
| Ash (%)* | 1.24 | 1.26 | 1.45 |
| ADF (%)* | 3.69 | 3.64 | 2.90 |
| NDF (%)* | 13.92 | 13.24 | 11.35 |
| Cellulose (%)* | 3.44 | 2.73 | 2.65 |
| Phosphorus (%)* | 0.28 | 0.26 | 0.31 |
| Starch (%)* | 64.76 | 64.67 | 71.73 |
| Beta Carotene (ug/100 g) | 18.2 | <0.05 | 107.5 |
| Xanthophyll (ug/100 g) | <1.0 | <0.08 | 4.08 |
| Fatty Acids (% of total fat) | | | |
| Myristic (14:0) | 0.12 | 0.03 | 0.00 |
| Myristoleic (14:1) | 0.08 | 0.00 | 0.00 |
| Palmitic (16:1) | 12.75 | 11.68 | 13.14 |
| Palmitoleic (16:1) | 0.23 | 0.13 | 0.12 |
| Stearic (18:0) | 2.83 | 1.93 | 1.94 |
| Oleic (18:1) | 25.53 | 22.43 | 23.77 |
| Linoleic (18:2) | 51.7 | 59.42 | 56.42 |
| Linolenic (18:3) | 1.29 | 1.06 | 1.80 |
| Arachidic (20:0) | 0.15 | 0.46 | 0.45 |
| Docosanoic (22:0) | 0.28 | 0.27 | 0.27 |
| Lignoceric (24:0) | 0.00 | 0.20 | 0.19 |

*Values are based on a 0% moisture basis

Total mass balance for all fractions was determined on dry basis.

Prior to wet milling, NIR analyses were performed on the grain, the results of which are shown in Table 6. The E8272 hybrid has higher protein and starch levels than the 1851W hybrid, and a lower oil content.

TABLE 6

Grain Properties of E8272 Verses 1851W

| Trait | E8272 | 1851W |
|---|---|---|
| NIR Protein Content (%, db) | 10.1 | 9.6 |
| NIR Starch Content (%, db) | 71.1 | 67.0 |
| NIR Oil Content (%, db) | 3.85 | 4.25 |
| Absolute Density (g/cc) | 1.302 | 1.285 |

The E8272 hybrid shows above average wet milling properties in comparison with other commercial hybrids. Mass balance calculated on dry basis shows that a 65.6% yield was obtained on the starch fraction, which falls on the high end of the range normally found among other white dent corn hybrids (64%+/−2%) using this laboratory procedure. The E8272 sample also yields a purer starch than is typically found among other white corn hybrids. The protein content of the starch was 0.35%, dry basis, which is much lower than values typically found among white corn hybrids (0.6%+/−0.2%). It was previously demonstrated on a commercial basis that the 1851W had excellent separation of starch from the protein. According to this data, E8272 wet milling properties follow a similar pattern to 1851W with the potential of generating even a higher level of starch purity.

The gluten meal obtained from the 1851W lab sample reveals a protein content (53.0%, dry basis) that is higher than typically found among other white dent corn varieties (45%+/−5%) using this lab procedure, see Table 7 and 8. These procedures identify the enhanced characteristics making the hybrids of this invention unique.

TABLE 7

Lab Wet Milling Material Balance of E8272 Verses 1851W

| Fraction | E8272 Yield (%, db) | 1851W Yield (%, db) |
|---|---|---|
| Starch | 65.6 | 65.2 |
| Gluten Meal | 9.3 | 8.8 |
| Germ | 8.1 | 9.7 |
| Coarse Fiber | 7.9 | 7.9 |
| Fine Fiber | 3.7 | 3.0 |
| Steep Water Solubles | 4.3 | 3.8 |
| Rinse Water Solubles | 1.0 | 1.2 |
| Total Solids | 99.9 | 99.6 |

TABLE 8

Product Quality of Solid Fractions

| Fraction | E8272 Protein (%, db) | 1851W Protein (%, db) | E8272 Oil (%, db) | 1851W Oil (%, db) |
|---|---|---|---|---|
| Starch | 0.35 | 0.42 | 0.059 | 0.046 |
| Gluten Meal | 45.6 | 53.0 | 2.42 | 1.74 |
| Germ | 13.3 | 14.2 | 39.4 | 40.7 |

EXAMPLE 3

Figure 1:
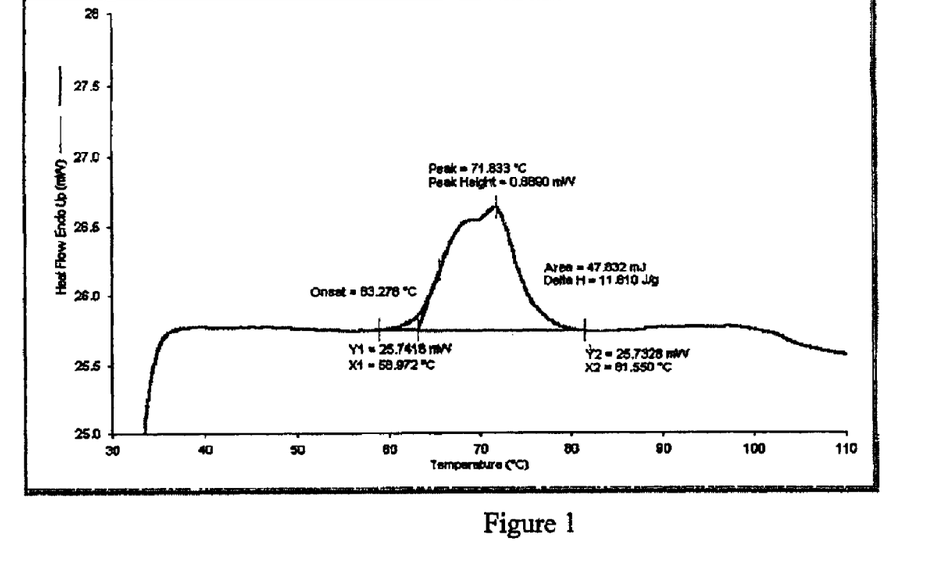
FIG. 1 shows the differential scanning calorimetry (DSC) profile for the 1851W starch.

This example illustrates the uniqueness of the pearl starch of 1851W and how it is positioned in the grain. Susan Duvick, manager of the USDA-ARS Quality Trait Analysis Laboratory looked at the structure and functionality of the starch from the 1851W hybrid that had been milled at the Iowa State University Center for Crops Utilization Research. The starch was gelatinized and stored for a week, then analyzed with differential scanning calorimetry (DSC) to measure how much energy was required to melt the crystallized starch. A typical corn starch generates a single, fairly uniform peak upon the same analysis. The DSC profile for the 1851W starch showed the starch gelled in two phases as shown in FIG. 1.

Figure 2:
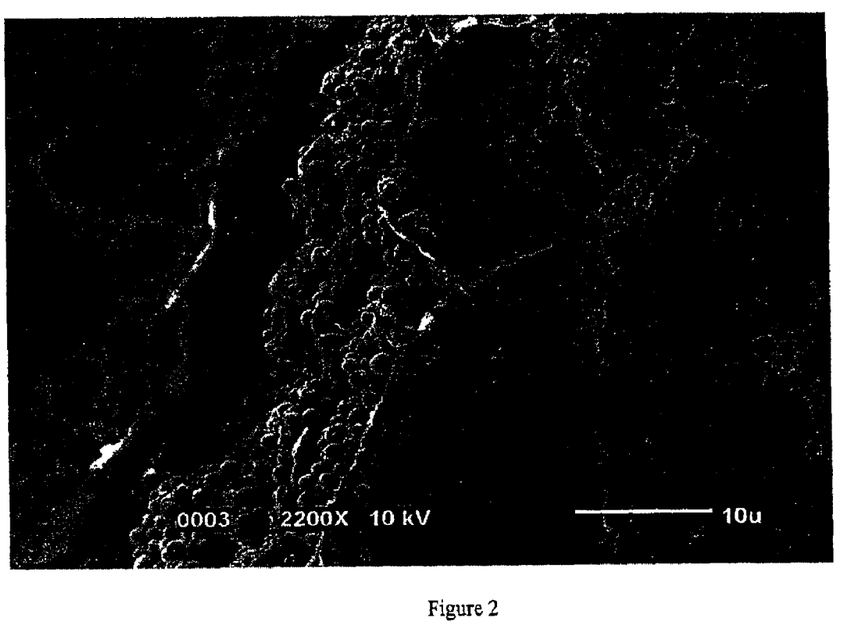
FIG. 2 illustrates an electron microgroup of the small, round granules found in the tip area of the 1851W kernel.
Figure 3:
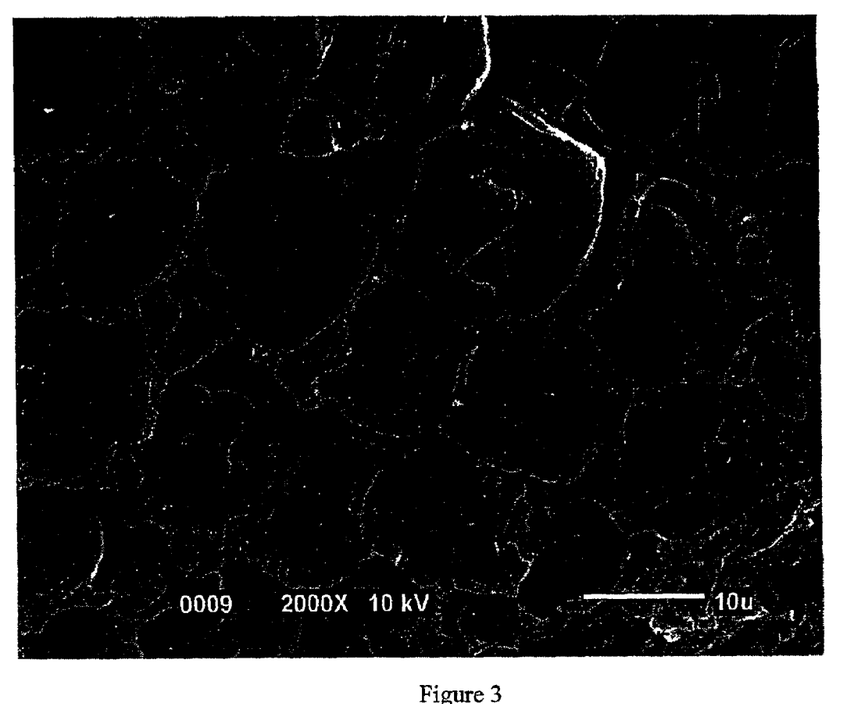
FIG. 3 is an electron micrograph of the crown section of 1851W kernel.

To account for the two thermal events, the starch granules were studied using electron micrography. A kernel of 1851W was freeze fractured and the starch granules were examined towards the tip and towards the crown of the kernel. Two distinct types of granules were found and they were distinctly separated according to location. In the tip area, small, round granules were found as shown in FIG. 2. Towards the crown, large, angular granules were found as shown in FIG. 3. Although typical corn starch exhibits a wide variety of granule shape and sizes, it does not express a distinct bimodality. Wheat starch, on the other hand, does exhibit this sort of bimodal starch granule composition with its large A- and small B-type granules. In wheat starch, the two types of starch granules do differ in their physical and chemical properties. The presence of the small, round granules at the tip end along with distinct channels provides an explanation for the rapid uptake of water in processing.

Analyses were conducted at USDA-ARS Quality Trait Analysis Laboratory, which examined the starch of E8272 from single kernel starch extraction, lab wet mill separation, and electron microscope examination of freeze fractured kernels.

The bench top single kernel procedure involves steeping the kernels of corn to soften the kernel, manually removing the pericarp and germ, grinding the kernel and pouring the slurry through a nylon mesh to filter out the fiber and large aggregates of endosperm and collect the starch and water in a beaker. The starch is allowed to settle and is washed several times to remove the residual protein and fiber. Starch settling rates were determined by measuring absorbency verses time. It was observed that the starch of 1851W settled faster than most other hybrids that indicated large, dense starch granules which was confirmed by the electron micrographs. When E8272 starch was compared to 1851W, it settled out even faster than 1851W as shown in Table 9.

TABLE 9

Starch Settling of Starch Measured by Absorbance

| Time (min.) | 1851W | E8272 |
|---|---|---|
| 1.0 | 1.590 | 1.528 |
| 2.0 | 1.581 | 1.528 |
| 4.0 | 1.555 | 1.427 |
| 6.0 | 1.386 | 1.126 |
| 8.0 | 1.141 | 0.847 |
| 10.0 | 0.931 | 0.650 |
| 12.0 | 0.773 | 0.506 |

Unexpectedly, examination of the starch granules of E8272 under an electron microscope revealed that the fast rate of settling for E8272 was not due to density but due to holes in the starch granules due to intrinsic enzyme activity. Starch granules with this type of configuration were not apparent in any of the other hybrids and certainly were not been observed in any conventional corn hybrids. This type of starch configuration could potentially be the next step in significantly reducing steep times in alkaline cooking or any other wet mill processing.

Grain of E8272 was analyzed in the laboratory for comparison to the 1851W model for making tortillas. The following treatments were used:

90° C. cooking temperature, 25 minute cooking time, with a 7 hour steep time

90° C. cooking temperature, 25 minute cooking time, with a 5 hour steep time

90° C. cooking temperature, 25 minute cooking time, with a 4 hour steep time

85° C. cooking temperature, 25 minute cooking time, with a 4 hour steep time

In treatment 1, the resulting masa was extremely wet and not useable for making tortillas. This indicated that the starch responded like the starch settling experiment where it absorbed water faster than 1851W. In treatment 2 and 3, the steep time was reduced, however, the masa was still too soft and sticky for sheeting. By reducing the temperature to 85° C. in treatment 4, high-quality tortillas could be made.

The alkaline cooking model indicates that E8272 can be cooked at much lower temperatures than normal (85° C. vs 95° C.), lower cook time (25 minutes vs 35 minutes), and use significantly less steep time (4 hours vs 12 hours).

EXAMPLE 4

This example illustrates the impact of the uniqueness of the 1851W starch and protein complex on alkaline cooking, and especially, tortilla production. Dr. David Jackson, at the University of Nebraska-Lincoln's Food Processing Center, developed a standardized, pilot-scale nixtamalization and tortilla production procedure in which proper quantification of input and output could be performed.

After a preliminary cooking test to determine the extremes in processing conditions, Dr. Jackson developed a central composite response surface design to determine the processing combinations that would be used for the study. In complex processes, such as tortilla cooking and processing, response surface experimental designs allow fewer trials to be run to understand a wide range of process conditions. When completed, the model serves as a graphic reference to determine optimum results. It may reveal, for example, the cooking and steeping processes that provide the lowest dry matter loss and result in good quality tortillas and tortilla chips. In addition, it could serve as a valuable tool for plant breeders to evaluate and screen new products without having to produce commercial quantities.

Following the resulting design, Jackson's group cooked corn while collecting data on a wide range of process parameters, including corn solids loss and distribution within cook, steep, and wash waters; yields of intermediate products and finished tortillas; and subjective observations of processing ease and tortilla quality.

A response surface model reflecting cooking and tortilla-making properties revealed that masa sheetability was higher for 1851W when cooked at temperatures less than 93° C. for cooking times similar to those for conventional food-grade hybrids, but for shorter steeping times (i.e., 10.5 hr of steeping compared with 12.0 hr for conventional food-grade corn). It was also discovered that for 1851W a product with higher dry matter (tortilla yield) could be achieved with steep times as short as 6 hr. Overall, the white corn hybrid displayed relative insensitivity to steep time compared with conventional hybrids.

Shortened steep times offer manufacturers of masa-based products several advantages. First, nixamalization, because it is a batch process, can be a manufacturing bottleneck. With shorter steep times, fewer tanks would be required at any given time, which would increase efficiency. In some operations, downstream forming, baking, and frying equipment may not be operating at full capacity. Under these conditions, a reduction in steep time might offer the potential to increase production capacity.

Steep tolerance could additionally offer another significant advantage in reducing waste when equipment fails. In addition, with a wide steep range, a processor might be able to enhance the robustness of the process by reducing cook times and extending the steep times.

Figure 4:
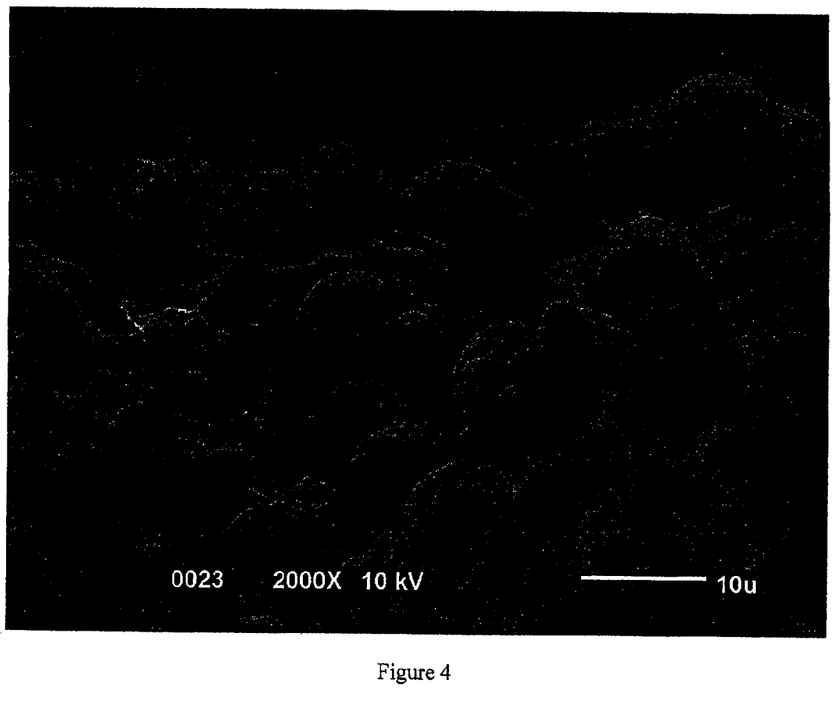
FIG. 4 is a chromatographic profile of the amylose and amylopectin of 1851W starch.

A chromatographic profile of the amylose and amylopectin was conducted on the 1851W starch by Dr. David Jackson at the University of Nebraska as shown in FIG. 4. The peak that comes out first is amylopectin followed by amylose. This is an unusual profile in that normally most corn starch can be easily separated by this technique. In the case of 1851W, there appears to be a range of starch polymers that fall within the full spectrum of amylose and amylopectin, and even into what would sometimes be called intermediate material.

Dr. David Jackson completed calculation estimates for amylose and amylopectin content of 1851W starch. The determined values at that time were 50.2% amylose and 49.8% amylopectin. However, the fact that in alkaline cooking 1851W required less steep time, reduced cook time, and reduced temperature, it was expected that there should be a higher amylopectin content. It was theorized that the branch chain lengths of the amylopectin starch in 1851W could be increased in length, and could possibly give a false reading for amylose.

Recently, Dr. Jay-Lin Jane at Iowa State University used gel permeation chromatography and iodine potentiometric titration to estimate the amylose and amylopectin content. Those results indicated the following:

| Hybrid | Amylose % | Amylopectin % |
|---|---|---|
| Standard Yellow | 35.1 | 64.9 |
| 1851W | 31.9 | 68.1 |
| E8272 | 30.0 | 70.0 |

By comparing the Blue Value of the iodine test to the total carbohydrate level, it was also estimated that the length of the amylopectin chains of 1851W starch are longer than normal.

In relative viscosity analysis (RVA), the starch had an initial peak viscosity 22% higher than commercial corn starch. Subsequent tests measured viscosity held at a constant temperature with stirring over a period of time. When compared with the results from commercial starch, the starch exhibited 31% higher viscosity after the holding period. With higher initial viscosity and better viscosity retention, the hybrid's starch may offer some of the properties of a modified starch without modification.

At the University of Illinois, Steve Echkoff and Yolanda Lopes created a small-scale laboratory procedure to quickly evaluate corn samples intended for use in masa and tortillas. Nine samples were evaluated using the procedure. The researchers cooked 100-gram samples of corn in Erylenmeyer flasks for a variety of cook times. After cooking, the corn was allowed to steep in the flasks at room temperature for 18 hr. After steeping, the researchers ground the masa, shaped it into a ball, and flattened it with a manual tortilla press. The resulting tortilla was baked and cooled. Both the masa and the finished tortilla were subjected to additional tests, including texture profile analysis (TPA). Used to evaluate tortilla-making potential, TPA measures qualities such as hardness, adhesiveness, cohesiveness, chewiness, gumminess, and springiness.

On the masa itself, the 1851W was among the few samples that absorbed close to the targeted minimum moisture content of 51% at the shortest cook time of 30 minutes. In addition, the hybrid exhibited a flatter response to changes in the cook time compared with the other sample.

Adhesiveness is measured as the total work required to release a cylinder of masa from the texture analyzer probe. Table 10 shows that masa adhesiveness increased with cook time for yellow corn hybrids while 1851W showed a decrease by almost 50% in going from a 30-minute cook time to a 90-minute cook time. Another Wilson Genetics white hybrid, 1780W, also decreased with cook time but to a lesser extent. Practical significance of adhesiveness is that too high of adhesion results in the masa sticking to the equipment and causing problems in the rolling and cutting operations. Too little adhesion results in brittle tortillas.

TABLE 10

Affect of cook time on masa adhesiveness for two yellow and two white corn hybrids.

| Cook Time (min.) | Masa Adhesiveness (g) | | | |
|---|---|---|---|---|
| | 1851W | 1780W | Standard Soft Yellow | Hard Endosperm Yellow |
| 30 | 110 | 72 | 44 | 8 |
| 60 | 82 | 50 | 58 | 21 |

TABLE 10-continued

Affect of cook time on masa adhesiveness for two yellow and two white corn hybrids.

| | Masa Adhesiveness (g) | | | |
|---|---|---|---|---|
| Cook Time (min.) | 1851W | 1780W | Standard Soft Yellow | Hard Endosperm Yellow |
| 90 | 62 | 60 | 78 | 45 |
| 120 | 70 | 38 | 90 | 63 |

Next, the texture analyzer measured the force and distance required to puncture the finished tortillas-an indication of tenderness. This force varied widely between the corn samples at the 30-minute cook time with the 1851W having the lowest puncture force required. In general, all hybrids tested decreased in puncture force with cook time. Most of the hybrids, however, required 90- to 120-minute cooking times to approach 1851W's tenderness at only 30 minutes of cooking time.

Cohesiveness is a measure of the strength of masa dough. The strength is determined as to how well the masa sample withstands a second compression (deformation) relative to the first compression. Low cohesiveness means that when the texture analyzer compresses the dough once, there is an internal disruption of the structure to the point that it takes little force to compress the dough further. The cohesiveness is thought to relate to the sheeting characteristics of masa dough and to the final thickness of the tortilla. Table 11 shows that 1851W hybrid was markedly different than the other hybrids. For the 1851W hybrid, cohesiveness decreased dramatically with cook time, while cohesiveness increased for the standard soft yellow corn. Basically, the results confirmed the trends that were found with the pilot-scale study in that 1851W responds differently than normal hybrids and it can reduce cook time, steep time, and cook temperature.

TABLE 11

Affect of cook time on cohesiveness for two yellow and two white corn hybrids.

| | Masa Cohesiveness Ratio | | | |
|---|---|---|---|---|
| Cook Time (min.) | 1851W | 1780W | Standard Soft Yellow | Hard Endosperm Yellow |
| 30 | 0.178 | 0.153 | 0.143 | 0.148 |
| 60 | 0.162 | 0.151 | 0.153 | 0.144 |
| 90 | 0.153 | 0.155 | 0.163 | 0.147 |
| 120 | 0.154 | 0.160 | 0.177 | 0.154 |

Although the uses of the present invention have been disclosed primarily with respect to foods and feed additives, this is not deemed to limit the scope of this invention. The present invention may be used in other fields of industry, e.g., paints, plastics, paper, wallboards. The present invention is embodied in hybrid corn having enhanced compositional characteristics and improved derivative products. Regardless of the specific application of the instant invention, the methodology details are calculated according to protocols well known in the art, as well as those disclosed herein. Further, the refinement of said necessary calculations is routinely made by those of ordinary skill in the art and is within the ambit of tasks routinely performed by them without undue experimentation.

While the above description contains much specificity, these specificities should not be construed as limitations on the scope of the invention, but rather exemplification of the preferred embodiment thereof. That is to say, the foregoing description of the invention is exemplary for purposes of illustration and explanation. Without departing from the spirit and scope of this invention, one skilled in the art can make various changes and modification to the invention to adapt it to various usages and conditions. As such, these changes and modification are properly, equitably and intended to be within the full range of equivalence of the following claims. Thus, the scope of the invention should be determined by the appended claims and their legal equivalents, rather than by the examples provided herein.

When made with masa from white corn, tortillas, tortilla chips and corn chips project a more upscale image to consumers. In the past, this image was well deserved because white corn commanded a higher price due to its lower yields. Today, seed companies have addressed white corn's yield issues and are focusing on adding value for food manufacturers. The Zimmerman Brand 1851W White Corn Hybrid from Wilson Genetics, L.L.C., Harlan, Iowa, for example, may actually help manufacturers of masa-based products reduce cost, improve production efficiency and increase manufacturing flexibility.

DEPOSIT INFORMATION

Deposit of the Wilson Genetics, LLC's corn inbreds WEBF428C and WICY418C disclosed above and recited in the appended claims has been made with the American Type Culture Collection (ATCC), 10801 University Boulevard, Manassas, Va. 20110. The date of deposit was Jan. 22, 2001. The deposit of 2,500 seeds were taken from the same deposit maintained by Wilson Genetics, LLC since prior to the filing date of this application. All restrictions upon the deposit have been removed, and the deposit is intended to meet all of the requirements of 37 C.F.R. '1.801–1.809. The ATCC accession numbers are PTA-2924 and PTA-2925 respectively. The deposit will be maintained in the depository for a period of 30 years, or 5 years after the last request, or for the effective life of the patent, whichever is longer, and will be replaced as necessary during that period.

We claim:

1. A method for extracting gluten protein of a white corn hybrid, comprising the steps of:
    a) selecting grain of a white corn hybrid producing by wet milling a gluten protein fraction comprising about 9% starch or less;
    b) wet milling said grain selected according to step a); and
    c) extracting the gluten protein fraction as a product of said wet milling of step b).

2. The method for extracting gluten protein according to claim 1, further comprising incorporating said gluten protein fraction, or a part thereof, into a white corn gluten feed.

3. The method for extracting gluten protein according to claim 1, further comprising incorporating said gluten protien fraction, or a part thereof into food products.

4. A method for extracting fiber from grain of a white corn hybrid comprising the steps of:
    a) selecting grain of a white corn hybrid producing by wet milling a fiber fraction comprising about 19% db protein or more;
    b) wet milling said grain selected according to step a); and
    c) extracting the fiber fraction as a product of said wet milling of step b).

5. The method for extracting fiber according to claim 4, further comprising incorporating said fiber fraction, or a portion thereof, into a white corn gluten feed.

6. The method for extracting fiber according to claim 4, further comprising incorporating said fiber fraction, or a portion thereof, into food products.

7. The method for extracting fiber according to claim 4, wherein said protein is about 70% soluble or greater.

8. A method for extracting gluten protein from grain of a white corn hybrid comprising the steps of:
   a. selecting grain of a white corn hybrid producing by wet milling a protein fraction of said grain that is about 73.0% db gluten nrotein or greater; and
   b. wet milling said grain selected according to step a); and
   c. extracting the gluten protein fraction as a product of said wet milling of step b).

9. The method for extracting gluten protein according to claim 8, further comprising incorporating said gluten protein fraction, or a portion thereof, into a white corn gluten feed.

10. The method for extracting gluten protein fraction according to claim 8, further comprising incorporating said gluten protein fraction, or a portion thereof, into food products.

* * * * *